United States Patent

Goldmann et al.

Patent Number: 5,162,338
Date of Patent: Nov. 10, 1992

[54] CIRCULATION ACTIVE 4-AMINOARYLDIHYDROPRYIDINE LACTONES

[75] Inventors: Siegfried Goldmann, Wuppertal; Matthias Schramm, Cologne; Rainer Gross, Wuppertal, all of Fed. Rep. of Germany; Günther Thomas, Milan, Italy; Martin Bechem, Wuppertal; Michael Kayser, Hagen, both of Fed. Rep. of Germany

[73] Assignee: Bayer Aktiengesellschaft, Leverkusen, Fed. Rep. of Germany

[21] Appl. No.: 782,748

[22] Filed: Oct. 18, 1991

Related U.S. Application Data

[63] Continuation of Ser. No. 260,823, Oct. 21, 1988, abandoned, which is a continuation of Ser. No. 944,405, Dec. 22, 1986, Pat. No. 4,804,667.

[30] Foreign Application Priority Data

Jan. 11, 1986 [DE] Fed. Rep. of Germany ....... 3600596

[51] Int. Cl.$^5$ .................... C07D 491/04; A61K 31/44
[52] U.S. Cl. ..................................... 514/302; 546/116
[58] Field of Search .......................... 514/302; 546/116

[56] References Cited

U.S. PATENT DOCUMENTS 4,284,634  8/1981  Satu ........................ 546/321
4,532,248  7/1985  Franckowiak et al. ........... 546/116

FOREIGN PATENT DOCUMENTS 0111453  6/1984  European Pat. Off. .
3130041  2/1983  Fed. Rep. of Germany .
3410645  9/1985  Fed. Rep. of Germany .

Primary Examiner—Jane T. Fan
Attorney, Agent, or Firm—Sprung Horn Kramer & Woods

[57] ABSTRACT

4 Aminoaryldihydropyridines of the formula

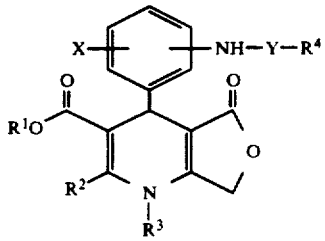

in which
R$^1$ is hydrogen or an organic radical, preferably methyl or ethyl,
R$^2$ is hydrogen, C$_1$-C$_5$- alkyl, —CN, —NH$_2$, —CH$_2$ or —CH$_2$OH, preferably methyl,
R$^3$ is hydrogen or alkyl, preferably hydrogen,
Y is —CO— or —SO$_2$—, and
R$^4$ is an organic radical, or
Y-R$^4$ is hydrogen, and physiologically acceptable salts thereof, are circulation-active and effective for improving myocardial contractility, for raising blood pressure, for lowering blood sugar, for reducing mucosal swelling and for controlling the salt and fluid balance.

12 Claims, No Drawings

CIRCULATION ACTIVE 4-AMINOARYLDIHYDROPRYIDINE LACTONES

This application is a continuation, of application Ser. No. 260,823, filed Oct. 21, 1988, now abandoned which is a continuation of Ser. No. 944,405, filed Dec. 22, 1986, now U.S. Pat. No. 4,804,667, issued Feb. 14, 1989.

The invention relates to 4-aminoaryl-dihydropyridine lactones, to process for their preparation and to their use in medicaments, in particular in medicaments affecting the circulation.

The present invention relates to new 4-aminoaryl-dihydropyridines of the general formula (I)

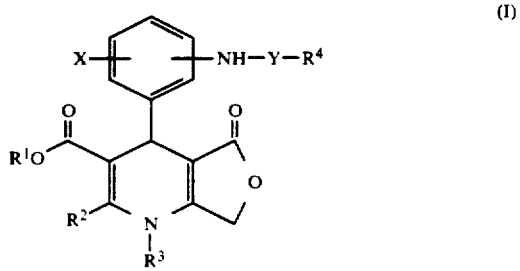

in which $R^1$ represents hydrogen or represents a straight-chain, branched or cyclic, saturated or unsaturated, hydrocarbon radical which has up to 15 carbon atoms and is optionally substituted by $C_1$-$C_{10}$-alkoxy, $C_1$-$C_{10}$-alkylthio, $C_1$-$C_{10}$-alkylsulphonyl, halogen, cyano, hydroxyl, morpholinyl, piperidyl, piperazinyl, by a group of the formula

in which $R^5$ and $R^6$ are identical or different and represent hydrogen, represent $C_1$-$C_{10}$-alkyl, represent $C_6$-$C_{14}$-aryl, represent $C_7$-$C_{14}$-aralkyl or represent $C_2$-$C_7$-acyl, or by an aryl or heteroaryl radical, the aryl or heteroaryl radicals optionally being substituted by 1 to 3 identical or different substituents from the group comprising halogen, $C_1$-$C_6$-alkyl, $C_1$-$C_6$-alkoxy, $C_1$-$C_6$-alkylthio, $C_1$-$C_6$-alkylsulfonyl, hydroxyl, cyano, nitro, amino, $C_1$-$C_6$-alkylamino, di-$C_1$-$C_6$-alkylamino, trifluoromethyl or trifluoromethoxy, $R^2$ represents $C_1$-$C_5$-alkyl, hydrogen, —CN, —NH$_2$, —CHO or —CH$_2$OH, $R^3$ represents hydrogen or represent straight-chain, branched or cyclic $C_1$-$C_6$-alkyl which is optionally substituted by morpholino, X represents hydrogen or represents halogen, Y represents the group

or —SO$_2$— and $R^4$ represents a straight-chain, branched or cyclic, saturated or unsaturated, hydrocarbon radical which has up to 20 C atoms and is optionally substituted by halogen, or represents $C_6$-$C_{14}$-aryl which is optionally substituted up to three times, identically or differently, by halogen, $C_1$-$C_8$-alkyl, $C_1$-$C_8$-alkoxy, $C_1$-$C_8$-alkylthio, $C_1$-$C_8$-halogenoalkyl having up to 5 halogen atoms, nitro, cyano, $C_1$-$C_8$-alkylsulphonyl or by the group

$R^7$ and $R^8$ having the meaning indicated for $R^5$ and $R^6$ and being identical to or different from the latter, or represents pyridyl, thienyl, furyl, pyrimidyl, pyrazinyl, quinolyl or isoquinolyl, each of which is optionally substituted by $C_1$-$C_6$-alkyl, $C_1$-$C_6$-alkoxy, halogen, cyano, nitro or di-$C_1$-$C_6$-alkylamino, or represents $C_7$-$C_{14}$-aralkyl, the aryl radical optionally being substituted by up to three identical or different substituents from the series comprising halogen, nitro, cyano, $C_1$-$C_4$-alkyl or $C_1$-$C_4$-alkoxy, or represents a group of the formula

$R^9$ and $R^{10}$ having the meaning indicated for $R^5$ and $R^6$ and being identical to or different from the latter, or the group —Y—$R^4$ denotes hydrogen, in the form of their isomers, isomer mixtures, racemates and optical antipodes, and to their physiologically acceptable salts.

The substances according to the invention have a good contractility-increasing and positive inotropic effect on the heart.

Preferred compounds of the general formula (I) are those in which $R^1$ represents a straight-chain, branched or cyclic aliphatic hydrocarbon radical which has up to 10 C atoms and is optionally substituted by $C_1$-$C_6$-alkoxy, $C_1$-$C_6$-alkylsulphonyl, one or more fluorine, chlorine, bromine, cyano or hydroxyl, by a group of the formula

in which $R^5$ and $R^6$ are identical or different and represent hydrogen, represent $C_1$-$C_6$-alkyl, represent phenyl or benzyl, or represent acetyl or benzoyl, or by phenyl, pyridyl, thienyl, furyl, pyrimidyl, quinolyl or isoquinolyl, it being possible for the phenyl and heteroaryl radicals to carry up to three identical or different substituents from the series comprising fluorine, chlorine, bromine, $C_1$-$C_4$-alkyl, $C_1$-$C_4$-alkoxy, cyano, nitro, di-$C_1$-$C_4$-alkylamino or trifluoromethyl, $R^2$ represents hydrogen, $C_1$-$C_5$-alkyl or —CN, $R^3$ represents hydrogen or represents straight-chain or branched $C_1$-$C_4$-alkyl, X represents hydrogen or represents fluorine, chlorine or bromine, Y represents the group

or —SO$_2$, and $R^4$ represents a straight-chain, branched or cyclic, saturated or unsaturated, hydrocarbon radical which has up to 15 carbon atoms and is optionally substituted by one or more fluorine or chlorine, or represents phenyl which is optionally substituted once to three times, identically or differently, by fluorine, chlorine, bromine, $C_1$-$C_6$-alkyl, $C_1$-$C_6$-alkoxy, $C_1$-$C_4$-halogenoalkyl having up to 5 halogen atoms, nitro, cyano, $C_1$-$C_4$-alkylsulphonyl or by a group of the formula

in which $R^7$ and $R^8$ have the meaning indicated for $R^5$ and $R^6$ and are identical to or different from the latter, or represents benzyl or phenethyl, or represents pyridyl, thienyl, furyl, quinolyl or pyrimidyl, each of which is optionally substituted by fluorine, chlorine, $C_1$-$C_4$-alkyl, $C_1$-$C_4$-alkoxy, cyano, nitro or dimethylamino, or represents the group

$R^9$ and $R^{10}$ having the meaning indicated for $R^5$ and $R^6$ and possibly being identical to or different from the latter, or the group —Y—$R^4$ denotes hydrogen, in the form of their isomers, isomer mixtures, racemates or optical antipodes and in the form of their physiologically acceptable salts.

Particularly preferred compounds of the formula (I) are those in which $R^1$ represents a straight-chain, branched or cyclic aliphatic hydrocarbon radical which has up to 6 carbon atoms and is optionally substituted by $C_1$-$C_3$-alkoxy, fluorine, chlorine, cyano, hydroxyl, the group of the formula

in which $R^5$ and $R^6$ are identical or different and represent hydrogen, represent $C_1$-$C_4$-alkyl, represent phenyl or benzyl, or represent acetyl, or by phenyl, pyridyl, quinolyl or pyrimidyl, it being possible for the phenyl and the heteroaryl radicals to be substituted by fluorine, chlorine, methyl, methoxy, cyano, nitro or trifluoromethyl, $R^2$ represents hydrogen, $C_1$-$C_4$-alkyl or cyano, $R^3$ represents hydrogen, X represents hydrogen or fluorine, Y represents the group

or —SO$_2$—, and $R^4$ represents a straight-chain, branched or cyclic alkyl or alkenyl radical which has up to 10 carbon atoms and is optionally substituted by one or more fluorine or chlorine, or represents phenyl which is optionally substituted up to twice, identically or differently, by fluorine, chlorine, $C_1$-$C_4$-alkyl, $C_1$-$C_4$-alkoxy, $C_1$-$C_4$-halogenoalkyl, nitro, cyano or by di-$C_1$-$C_4$-alkylamino, or represents benzyl, or represents pyridyl, furyl, thienyl or quinolyl, each of which is optionally substituted by fluorine, chlorine, methyl, methoxy or nitro, or represents the group of the formula

in which $R^9$ and $R^{10}$ have the meaning indicated for $R^5$ and $R^6$ and are identical to or different from the latter, or the group —Y—$R^4$ denotes hydrogen, in the form of their isomers, isomer mixtures, racemates or optical antipodes and in the form of their physiologically acceptable salts.

The substances according to the invention can exist in the form of their salts. In general, these are salts of the substances according to the invention with inorganic or organic acids. However, the physiologically acceptable salts of the substances according to the invention with inorganic and organic acids are preferred. Examples which may be mentioned are: hydrohalides, hydrogen sulphates, sulphates, hydrogen phosphates, acetates, maleates, citrates, fumarates, tartrates, lactates or benzoates.

The compounds according to the invention exist in stereoisomeric forms which either are related as image and mirror image (enantiomers) or are not related as image and mirror image (diastereomers). The invention relates to both the antipodes and the racemic forms as well as mixtures of diastereomers. The racemic forms can be resolved in exactly the same way as the mixtures of diastereomers into the stereoisomerically homogeneous constituents in a known manner (compare E. L. Eliel, Stereochemistry of Carbon Compounds, Mc Graw Hill, 1962).

The compounds of the general formula (I) according to the invention are obtained when nitro compounds of the general formula (II)

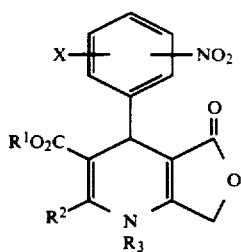
(II)

in which

R¹, R², R³ and X have the abovementioned meaning, are reduced, where appropriate in the presence of a catalyst, where appropriate in the presence of an acid, and where appropriate in the presence of an inert solvent, in a manner known per se to give amino compounds of the general formula (III)

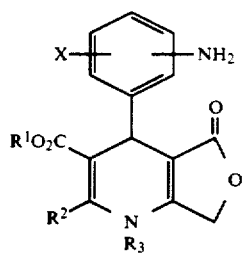
(III)

in which

R¹, R², R³ and X have the abovementioned meaning, and, where appropriate in a second step, the compounds of the formula (III) are reacted with compounds of the general formula IV $$R^4-Y-Z \quad (IV)$$

in which

R⁴ and Y have the abovementioned meaning, and Z represents halogen, preferably chlorine or bromine, or represents a group —O—Y—R⁴, where appropriate in the presence of a base, and where appropriate in the presence of an inert solvent.

When the starting materials used are methyl 2-methyl-4-(3-nitrophenyl)-5-oxo-1,4,5,7-tetrahydrofuro[3,4-b]pyridine-3-carboxylate and benzoyl chloride or p-tosyl chloride, the reaction can be illustrated by the diagram which follows:

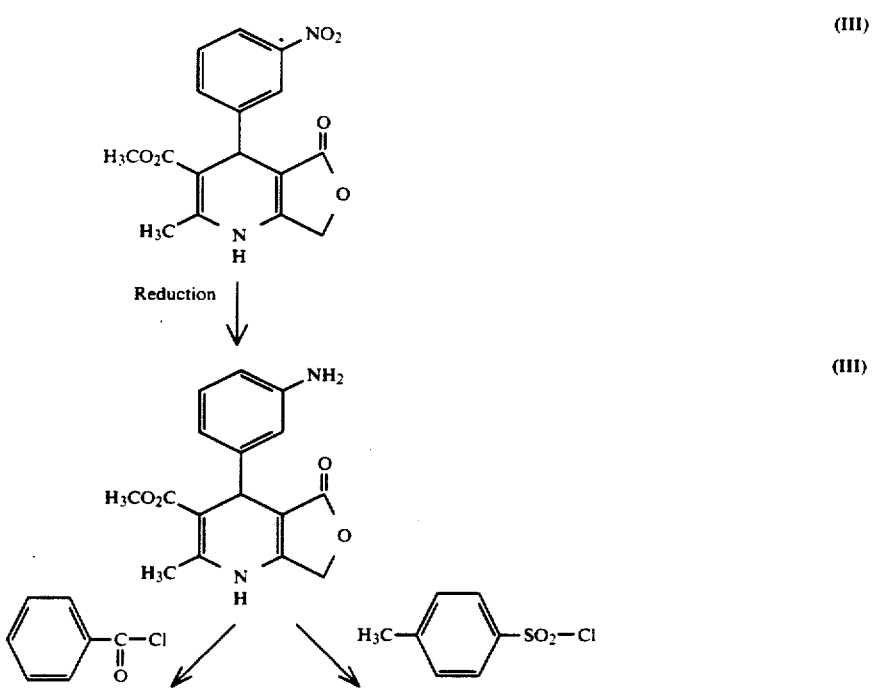

-continued

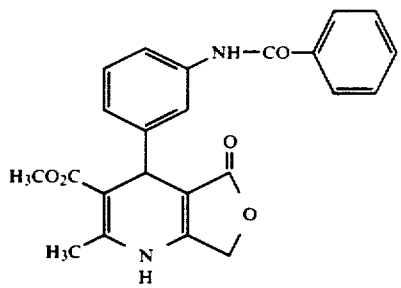
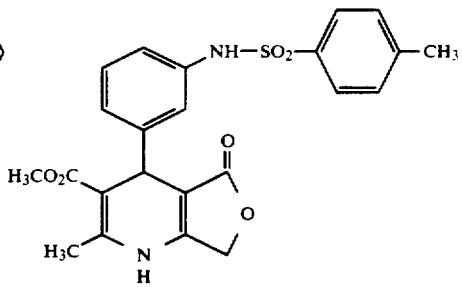

The compounds of the formula (II) which are used as starting materials are known or can be prepared by known methods (DE-OS (German Published Specification) 3,206,671).

The reduction in the first reaction step is carried out in a manner known per se, preferably by hydrogenation using metal catalysts such as, for example, platinum, palladium, palladium on animal charcoal or Raney nickel in the presence of acids.

The acids which can be used according to the invention are strong mineral acids as well as organic acids. Hydrogen halide acids such as HCl or HBr, sulphuric acid, phosphoric acid, perchloric acid, acetic acid, trifluoroacetic acid or p-toluenesulphonic acid are preferred.

The catalyst for this is generally used in an amount of 0.1 to 50 mol-%, preferably of 1 to 10 mol-%, relative to the nitro compound.

The hydrogenation is generally carried out in the temperature range from $-20°$ to $+100°$ C., preferably in the range from $0°$ to $+50°$ C.

In general, the hydrogenation is carried out with an excess pressure of 5 to 100 bar, preferably of 10 to 80 bar. It is equally possible to carry out the hydrogenation under atmospheric pressure.

Suitable solvents for the hydrogenation are water and/or inert organic solvents. These preferably include alcohols such as methanol, ethanol, propanol or isopropanol, ethers such as diethyl ether, dioxane, tetrahydrofuran, glycol monomethyl ether or glycol dimethyl ether, chlorinated hydrocarbons such as methylene chloride, chloroform or carbon tetrachloride, glacial acetic acid, dimethylformamide, ethyl acetate or acetone. It is equally possible to use mixtures of the said solvents.

The reduction is particularly preferably carried out with Raney nickel in alcohols with an excess pressure of hydrogen.

However, it is equally possible to carry out the reduction with metals such as zinc, tin or iron in the presence of acids such as acetic acid or hydrochloric acid as described by R. Schröter in Houben-Weyls "Methoden der organischen Chemie" ("Methods of Organic Chemistry") XI/1, pages 363 et seq.

Suitable solvents in the second reaction step are inert organic solvents which are not changed under the reaction conditions. These preferably include ethers such as diethyl ether, dioxane, tetrahydrofuran, glycol monomethyl ether or glycol dimethyl ether, chlorinated hydrocarbons such as methylene chloride, chloroform, carbon tetrachloride or 1,2-dichloroethane, or hydrocarbons such as benzene, toluene, xylene, hexane or petroleum fractions. It is equally possible to use mixtures of the said solvents.

Suitable bases are the customary organic bases. These preferably include trialkylamines such as triethylamine or pyridine, quinoline, isoquinoline, methylpiperidine or methylmorpholine. It is equally possible to use inorganic bases such as sodium or potassium carbonate, as well as alcoholates such as sodium ethylate, sodium methylate, potassium ethylate or potassium methylate. Triethylamine is particularly preferably used.

The reaction is carried out in a temperature range from $0°$ C. to $100°$ C., preferably from $10°$ to $50°$ C.

The reaction can be carried out under atmospheric pressure as well as under elevated or reduced pressure. In general, it is carried out under atmospheric pressure.

The compounds according to the invention exhibit a valuable spectrum of pharmacological actions which could not have been predicted. They can be used as cardiotonics for improving myocardial contractility. Furthermore, they can be used as antihypotensives, for lowering blood sugar, for reducing mucosal swelling and for influencing the salt and fluid balance.

The action increasing myocardial contractility was found in isolated atria of guineapig hearts.

For this purpose, the left atria of guineapig hearts are isolated and suspended in a thermostated organ bath which contains an isotonic mineral salt solution which is adjusted to the ionic environment and the pH of body fluids and contains suitable nutrients. A gas mixture consisting of oxygen and carbon dioxide was passed through this organ bath, the carbon dioxide content being adjusted so that the pH of the organ bath remains constant. The left atria were clamped in the organ bath, and the tension was recorded by a force sensor, a particular basic tone being set up. Then the left atria received continual electrical stimuli at set intervals, and the contractions taking place during this were recorded. At a concentration of $10^{-6}$ g/ml there is an increase in contractility compared with the initial figure which is set equal to 100%.

| Compound of Example No. | Increase in contractility at $10^{-6}$ g/ml |
|---|---|
| 6 | +47% |
| 7 | +80% |
| 8 | +42% |
| 28 | +33% |
| 29 | +140% |

The new active compounds can be converted in a known manner into the customary formulations, such as tablets, capsules, coated tablets, pills, granules, aerosols, syrups, emulsions, suspensions and solutions, using inert, non-toxic, pharmaceutically suitable vehicles or solvents. The therapeutically active compounds should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil, alcohols (for example ethyl alcohol and glycerol) and glycols (for example propylene glycol and polyethylene glycol), solid vehicles, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodiumlaurylsulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can also be used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.001 to 1 mg/kg, preferably about 0.01 to 0.5 mg/kg, body weight to achieve effective results, and in the case of oral administration, the dosage is about 0.01 to 20 mg/kg, preferably 0.1 to 10 mg/kg, body weight.

Nevertheless, it can at times be necessary to deviate from the amounts mentioned, and in particular to do so as a function of the body weight of the experimental animal or of the nature of the administration method, but also because of the species of animal and its individual behavior towards the medicament, or the nature of the formulation of the medicament and the time or interval over which the administration takes place. Thus it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

PREPARATION EXAMPLES

EXAMPLE 1

Ethyl 4-(2-aminophenyl)-2-methyl-5-oxo-1,4,5,7-tetrahydrofuro[3,4-b]pyridine-3-carboxylate

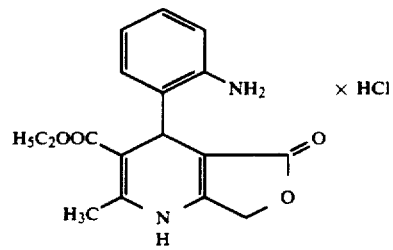

58 mmol of ethyl 4-(2-nitrophenyl)-2-methyl-5-oxo-1,4,5,7-tetrahydrofuro[3,4-b]pyridine-3-carboxylate are dissolved in 200 ml of tetrahydrofuran, and 2 g of Raney nickel are added. Hydrogenation is carried out under a pressure of 50 bar of $H_2$ for 1.5 h. The solution is evaporated, and dilute hydrochloric acid is added and the product is filtered off with suction and dried. Yield: 56% of theory Melting point: 175°–183° C.

The following were prepared in analogy to Example 1:

EXAMPLE 2

Methyl 4-(2-aminophenyl)-2-methyl-5-oxo-1,4,5,7-tetrahydrofuro[3,4-b]pyridine-3-carboxylate

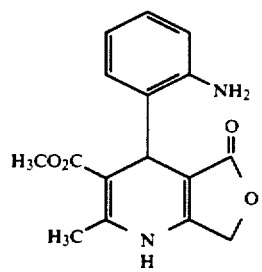

Yield: 80% of theory
Melting point: 193°–5° C.

EXAMPLE 3

Butyl 4-(2-aminophenyl)-2-methyl-5-oxo-1,4,5,7-tetrahydrofuro[3,4-b]pyridine-3-carboxylate

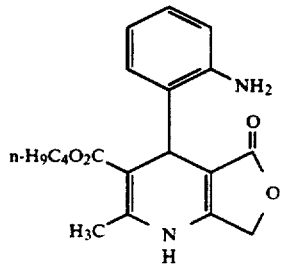

Yield: 60% of theory

Melting point: 167°-9° C.

EXAMPLE 4

Ethyl 4-(3-aminophenyl)-2-methyl-5-oxo-1,4,5,7-tetrahydrofuro[3,4-b]pyridine-3-carboxylate

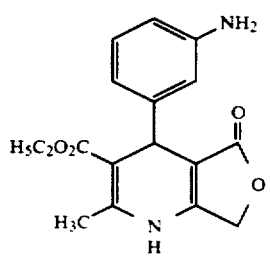

Yield: 80% of theory

Melting point: 179°-181° C.

EXAMPLE 5

Ethyl 4-(2-benzoylamino)-2-methyl-5-oxo-1,4,5,7-tetrahydrofuro[3,4-b]pyridine-3-carboxylate

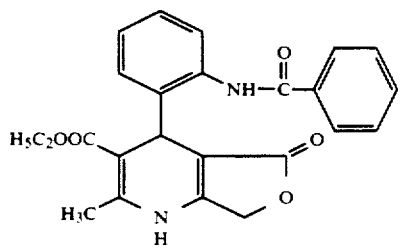

10 mmol of ethyl 4-(2-aminophenyl)-2-methyl-5-oxo-1,4,5,7-tetrahydrofuro[3,4-b]pyridine-3-carboxylate are dissolved in 100 ml of $CH_2Cl_2$, and 3 3 ml of triethylamine (20 mmol) are added. 10 mmol of benzoyl chloride are added to this solution. The mixture is stirred at room temperature for 1.5-2.0 hours. The solution is extracted by shaking 1× with $H_2O$, and the organic phase is dried with $Na_2SO_4$ or a molecular sieve and is evaporated. Crystals are obtained from methanol or ethanol.

Yield: 80% of theory

Melting point: 275° C.

The examples in the tables which follow were prepared in analogy to Example 5:

TABLE 1

| Example No. | $R^1$ | $R^3$ | X | Y | $R^4$ | Melting point [°C.] |
|---|---|---|---|---|---|---|
| 6 | $CH_3$ | H | H | CO | 4-chlorophenyl | >270 |
| 7 | $CH_3$ | H | H | CO | phenyl | >270 |
| 8 | $CH_3$ | H | H | CO | 3-chlorophenyl | >270 |
| 9 | $CH_3$ | H | H | CO | 2-methylphenyl | 235-6 |
| 10 | $CH_3$ | H | H | CO | 4-methylphenyl | 220-2 |
| 11 | $CH_3$ | H | H | CO | 3-methylphenyl | >270 |
| 12 | $CH_2CH_3$ | H | H | $SO_2$ | 4-methylphenyl | 115-20 |
| 13 | $CH_2CH_3$ | H | H | CO | —NH-phenyl | 233-7 |
| 14 | $CH_2CH_3$ | H | H | CO | —$CH_2$-phenyl | >250 |

TABLE 1-continued

[Structure: 4-aryl-dihydropyridine fused with furanone; aryl bearing X and NH-Y-R⁴ substituents; R¹O₂C and CH₃ on pyridine ring; N-R³]

| Example No. | R¹ | R³ | X | Y | R⁴ | Melting point [°C] |
|---|---|---|---|---|---|---|
| 15 | CH₂CH₃ | H | H | CO | 3-methylphenyl | >250 |
| 16 | CH₂CH₃ | H | H | CO | 4-methylphenyl | >250 |
| 17 | CH₂CH₃ | H | H | CO | 3-chlorophenyl | >250 |
| 18 | CH₂CH₃ | H | H | CO | 4-chlorophenyl | >250 |
| 19 | CH₂CH₃ | H | H | CO | CH₂CH₃ | >250 |
| 20 | CH₂CH₃ | H | H | CO | —CH₂—CH(CH₃)₂ | 228–30 |
| 21 | CH₂CH₃ | H | H | CO | cyclohexyl | 183–5 |
| 22 | CH₂CH₃ | H | H | CO | —(CH₂)₇CH₃ | 167–70 |
| 23 | CH₂CH₃ | H | H | CO | 4-methoxyphenyl | >250 |
| 24 | CH₂CH₃ | H | H | CO | 4-nitrophenyl | >250 |
| 25 | CH₂CH₃ | H | H | CO | 2,3-dimethylphenyl (H₃C at ortho) | >250 |
| 26 | CH₂CH₃ | H | H | CO | 4-tert-butylphenyl | >250 |
| 27 | CH₂CH₃ | H | H | CO | 4-(CH₂Cl)phenyl | >250 |
| 28 | CH₂CH₃ | H | H | CO | 2-fluorophenyl | >250 |
| 29 | CH₂CH₃ | H | H | CO | 4-pyridyl | >250 |
| 30 | CH₂CH₃ | H | H | CO | 4-(CF₃)phenyl | >250 |
| 31 | n-C₄H₉ | H | H | CO | 3-chlorophenyl | 232–5 |
| 32 | n-C₄H₉ | H | H | CO | 4-chlorophenyl | 225–7 |
| 33 | n-C₄H₉ | H | H | CO | phenyl | 148–55 |
| 34 | n-C₄H₉ | H | H | CO | 3-methylphenyl | 225–27 |

TABLE 1-continued

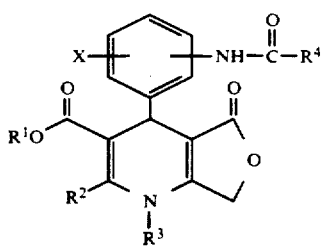

| Example No. | $R^1$ | $R^3$ | X | Y | $R^4$ | Melting point [°C] |
|---|---|---|---|---|---|---|
| 35 | n-C$_4$H$_9$ | H | H | CO | (3-methylphenyl) | 203-4 |
| 36 | n-C$_4$H$_9$ | H | H | CO | (4-methylphenyl) | 234-6 |

TABLE 2

| Example No. | $R^1$ | $R^3$ | X | Y | $R^4$ | Melting point [°C] |
|---|---|---|---|---|---|---|
| 37 | C$_2$H$_5$ | H | H | CO | phenyl | 252-3 |
| 38 | C$_2$H$_5$ | H | H | CO | (3-methylphenyl) | 225-8 |
| 39 | C$_2$H$_5$ | H | H | CO | (4-methylphenyl) | 251-6 |

It will be understood that the specification and examples are illustrative but not limitative of the present invention and that other embodiments within the spirit and scope of the invention will suggest themselves to those skilled in the art.

We claim:

1. A 4-aminoaryldihydropyridine of the formula in which $R^1$ represents hydrogen or alkyl which has up to 15 carbon atoms and is optionally substituted by C$_1$–C$_{10}$-alkoxy or C$_1$–C$_{10}$-alkylthio, $R^2$ represents hydrogen, C$_1$–C$_5$-alkyl, —CN, —NH$_2$, —CHO or —CH$_2$OH, $R^3$ represents hydrogen or represent straight-chain, branched or cyclic alkyl of up to 6 carbon atoms, X represents hydrogen or represents halogen, and $R^4$ represents a straight-chain, branched or cyclic alkyl radical which has up to 20 C atoms and is optionally substituted by halogen, or a physiologically acceptable salt thereof.

2. A 4-aminoaryldihydropyridine or salt according to claim 1, in which $R^1$ represents alkyl which has up to 10 C atoms and is optionally substituted by C$_1$–C$_6$-alkoxy, $R^2$ represents hydrogen, C$_1$–C$_5$-alkyl or —CN, $R^3$ represents hydrogen or represents straight-chain or branched C$_1$–C$_4$-alkyl, X represents hydrogen or represents fluorine, chlorine or bromine, and $R^4$ represents a straight-chain, branched or cyclic alkyl radical which has up to 15 carbon atoms and is optionally substituted by one or more of fluorine or chlorine.

3. A 4-aminoaryldihydropyridine or salt according to claim 1, in which $R^1$ represents alkyl which has up to 6 C atoms and is optionally substituted by C$_1$–C$_3$-alkoxy, $R^2$ represents hydrogen, C$_1$–C$_4$-alkyl or —CN, $R^3$ represents hydrogen, X represents hydrogen or represents fluorine, and $R^4$ represents a straight-chain, branched or cyclic alkyl radical which has up to 10 carbon atoms and is optionally substituted by one or more of fluorine or chlorine.

4. A 4-aminoaryldihydropyridine according to claim 1, wherein such compound is ethyl 4-(2-isovaleroylamino-phenyl)-2-methyl-5-oxo-1,4,5,7-tetrahydrofuro[3,4-b]pyridine-3-carboxylate of the formula

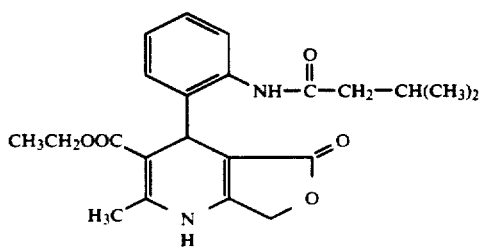

or a physiologically acceptable salt thereof.

5. A compound according to claim 1, wherein such compound is ethyl 4-(2-propionylamino-phenyl)-2-methyl-5-oxo-1,4,5,7-tetrahydrofuro[3,4-b]pyridine-3-carboxylate of the formula

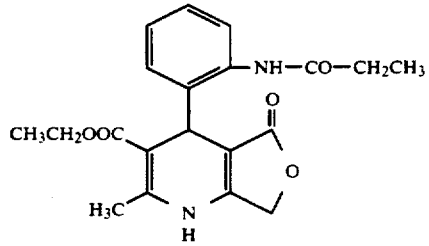

or a physiologically acceptable salt thereof.

6. A compound according to claim 1, wherein such compound is ethyl 4-(2-isovaleroylamino-phenyl)-2-methyl-5-oxo-1,4,5,7-tetrahydrofuro[3,4-b]pyridine-3-carboxylate of the formula

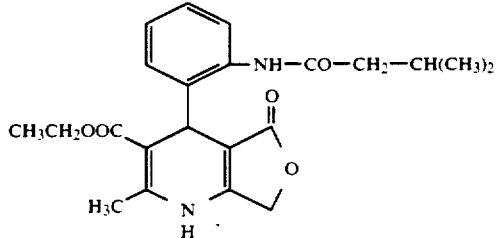

or a physiologically acceptable salt thereof.

7. A compound according to claim 1, wherein such compound is ethyl 4-(2-cyclohexancarbonylamino-phenyl)-2-methyl-5-oxo-1,4,5,7-tetrahydrofuro[3,4-b]pyridine-3-carboxylate of the formula

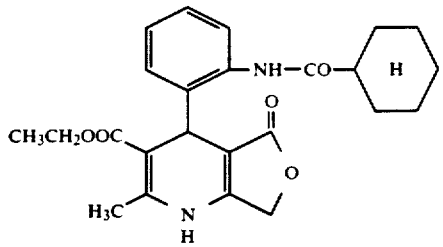

or a physiologically acceptable salt thereof.

8. A compound according to claim 1, wherein such compound is ethyl 4-(2-nonanoylamino-phenyl)-2-methyl-5-oxo-1,4,5,7-tetrahydrofuro[3,4-b]pyridine-3-carboxylate of the formula

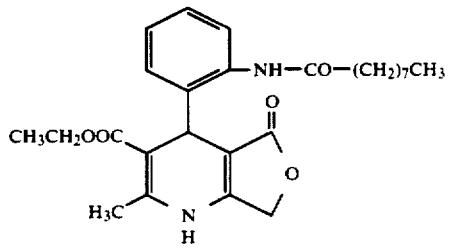

or a physiologically acceptable salt thereof.

9. A composition for improving myocardial contractility which comprises an amount effective therefor of a compound or salt according to claim 1 and a diluent.

10. A unit dose of a composition according to claim 9, in the form of a tablet, capsule or ampule.

11. A method of improving myocardial contractility in a patient in need thereof, which comprises administering to such patient an amount effective therefor of a compound or salt according to claim 1.

12. The method according to claim 11, wherein such compound is
ethyl 4-(2-isovaleroylamino-phenyl)-2-methyl-5-oxo-1,4,5,7-tetrahydrofuro[3,4-b]pyridine-3-carboxylate.

* * * * *

UNITED STATES PATENT AND TRADEMARK OFFICE
CERTIFICATE OF CORRECTION

PATENT NO. : 5,162,338
DATED : November 10, 1992
INVENTOR(S) : Goldmann, et. al.

It is certified that error appears in the above-indentified patent and that said Letters Patent is hereby corrected as shown below:

Title page, item [54] and col. line 2, should read -- "AMINOARYLDIHYDROPYRIDINE" --..

Signed and Sealed this

Ninth Day of August, 1994

Attest:

BRUCE LEHMAN

Attesting Officer

Commissioner of Patents and Trademarks